(12) United States Patent
Cho et al.

(10) Patent No.: US 12,734,014 B2
(45) Date of Patent: Sep. 15, 2026

(54) HOLDER FOR MEDICAL TOOLS

(71) Applicant: CUREXO, INC., Seoul (KR)

(72) Inventors: Gyu Il Cho, Seoul (KR); Heung Soon Lim, Seoul (KR); Bong Oh Kim, Seoul (KR)

(73) Assignee: CUREXO, INC., Seoul (KR)

( * ) Notice: Subject to any disclaimer, the term of this patent is extended or adjusted under 35 U.S.C. 154(b) by 0 days.

(21) Appl. No.: 19/118,680

(22) PCT Filed: Sep. 20, 2023

(86) PCT No.: PCT/KR2023/014311
§ 371 (c)(1),
(2) Date: Apr. 4, 2025

(87) PCT Pub. No.: WO2024/076054
PCT Pub. Date: Apr. 11, 2024

(65) Prior Publication Data

US 2026/0130741 A1 May 14, 2026

(30) Foreign Application Priority Data

Oct. 5, 2022 (KR) ........................ 10-2022-0126766

(51) Int. Cl.
*A61B 90/50* (2016.01)
*A61B 17/92* (2006.01)
*A61B 90/00* (2016.01)

(52) U.S. Cl.
CPC .............. *A61B 90/50* (2016.02); *A61B 17/92* (2013.01); *A61B 90/03* (2016.02)

(58) Field of Classification Search
CPC ......... A61B 90/50; A61B 90/03; A61B 17/92; A61B 17/58; A61B 17/16; A61B 17/1684; A61B 17/1655; A61B 17/1664; A61B 17/1666; A61B 17/1668; A61B 34/30
See application file for complete search history.

(56) References Cited

U.S. PATENT DOCUMENTS 8,753,346 B2 6/2014 Suarez et al.
2011/0082462 A1* 4/2011 Suarez .............. A61B 17/1684 606/130

FOREIGN PATENT DOCUMENTS

| CN | 111528977 A | 8/2020 |
| --- | --- | --- |
| JP | 2019-533491 A | 11/2019 |
| KR | 10-2012-0066980 A | 6/2012 |
| KR | 10-2016-0039695 A | 4/2016 |
| KR | 10-1685083 B1 | 12/2016 |

(Continued)

*Primary Examiner* — Christopher J Beccia
(74) *Attorney, Agent, or Firm* — Bridgeway IP Law Group, PLLC; Jihun Kim

(57) ABSTRACT

An embodiment relates to a holder for medical tools, to which an impactor, a reamer, etc. used in a surgical operation is mounted, and more specifically, to a holder for medical tools, which has a concise and simple structure, satisfies operational stability and durability, and is usable interchangeably. The holder for medical tools includes: a medical tool including a tool shaft; a holder main body internally formed with a tool mounting hole to insert the medical tool therein; and a tool supporting means supporting the medical tool inserted in the holder main body, wherein the tool supporting means includes a tool support guide member to guide movement of the tool shaft while supporting the tool shaft.

11 Claims, 13 Drawing Sheets

(56) References Cited

FOREIGN PATENT DOCUMENTS

| | | | |
|---|---|---|---|
| KR | 10-2020-0115518 | A | 10/2020 |
| KR | 10-2020-0136201 | A | 12/2020 |
| KR | 10-2415277 | B1 | 6/2022 |

* cited by examiner

<a>

<b>

<c>

HOLDER FOR MEDICAL TOOLS

TECHNICAL FIELD

The disclosure relates to a holder for medical tools, to which an impactor, a reamer, etc. used in a surgical operation is mounted, and more specifically, to a holder for medical tools, which has a concise and simple structure, satisfies operational stability and durability, and is usable interchangeably.

BACKGROUND ART

In general, surgical treatment for joint diseases includes arthroscopic surgery, chondrocyte transplantation, etc. and includes artificial joint surgery for severe conditions. As representative artificial joint surgery, there are manual artificial joint surgery manually performed by medical personnel, and robotic artificial joint surgery performed by a robot.

The robotic artificial joint surgery refers to a surgical procedure of placing an artificial joint (or implant) after cutting a bone from a joint area by rotating a cutter of a cutting device mounted to a distal end of a position-variable arm of the robot based on information input to a computer, and employs a cutting tool such as a drill, a reamer for widening a drilled hole, and an impactor for providing a press-fitting force.

The artificial joint surgery is common in artificial knee joint surgery, and artificial hip joint surgery has recently been also gradually increasing.

The artificial hip joint surgery is usually performed by preprocessing an acetabulum of a hip joint using the reamer, inserting an artificial acetabulum-cup, pressing and fitting the artificial acetabulum-cup using the impactor, and then connecting an artificial femoral head.

Meanwhile, the reamer includes a straight reamer, the outer appearance of which is shaped to have a straight structure, and a curved reamer (or offset reamer), the outer appearance of which is shaped to have a curved structure.

In addition, the impactor includes a straight impactor, the outer appearance of which is shaped to have a straight structure, and a curved impactor, the outer appearance of which is shaped to have a curved structure.

As described above, the artificial hip joint surgery needs various surgical tools such as the straight reamer, the offset reamer, the straight impactor, and the curved impactor during surgery, thereby requiring a medical tool holder capable of stably holding the surgical tools and being interchangeably usable.

As such a holder for medical tools, there have been proposed technologies such as Korean Patent No. 10-1609281, registered on Mar. 30, 2016 and titled 'TOOL, KIT-OF-PARTS FOR MULTI-FUNCTIONAL TOOL, AND ROBOTIC SYSTEM FOR SAME,' but these technologies have disadvantages of increasing manufacturing and maintenance costs due to excessively many components and structural complexity, and disadvantages of hindering reliable surgery due to a high possibility of failure.

Besides, the conventional holder for medical tools has problems as follows. In the process of installing the impactor and striking the impactor to perform a procedure by a medical man, if the striking direction of the hammer is misaligned with the longitudinal direction, i.e., axial direction of the impactor to apply an impact force to the impactor in an oblique direction (i.e., wrong direction), the holder and the impactor may be broken or damaged.

In addition, when the hammer misses the impactor, the impact force is obliquely applied even to the artificial acetabulum-cup, thereby not only having an adverse effect on the surgery but also causing injury or damage to a medical man (or robot) as the impact force of the hammer is transmitted to the medical man who (or the robot that) holds the holder.

DOCUMENTS OF RELATED ART

Patent Documents (Patent document 1) Korean Patent Publication No. 10-2020-0115518, titled "end effectors, systems, and method for impacting prosthetics guided by surgical robots"

(Patent document 2) U.S. Pat. No. 8,753,346B2, titled "TOOL, KIT-OF-PARTS FOR MULTI-FUNCTIONAL TOOL, AND ROBOTIC SYSTEM FOR SAME"

(Patent document 3) Korean Patent Publication No. 10-2020-0115518, titled "END EFFECTORS, SYSTEMS, AND METHODS FOR IMPACTING PROSTHETICS GUIDED BY SURGICAL ROBOTS"

DISCLOSURE

Technical Problem

The disclosure has been conceived based on the foregoing description, and an aspect of the disclosure is to provide a holder for medical tools, which has a concise and simple structure, satisfies operational stability and durability, and is usable interchangeably.

Another aspect of the disclosure is to provide a holder for medical tools, which absorbs and buffers abnormal impact applied to the medical tool.

Technical Solution

According to an aspect of the disclosure, a holder for medical tools includes: a medical tool including a tool shaft; a holder main body internally formed with a tool mounting hole to insert the medical tool therein; and a tool supporting means supporting the medical tool inserted in the holder main body, wherein the tool supporting means includes a tool support guide member to guide movement of the tool shaft while supporting the tool shaft.

The tool support guide member may include a sliding support body that has an outer circumferential surface to couple with an inner circumferential surface of the tool mounting hole, and an inner circumferential surface into which the tool shaft is inserted.

In addition, the holder may further include a holder supporting member coupled to the holder main body.

The tool mounting hole may include: a guide member installation groove formed on an inner circumferential surface thereof to seat the tool support guide member thereon; a support member installation groove formed in contact with the guide member installation groove to install a holder connecting member for installation of the holder supporting member; and a tool installation groove formed at one end portion of the tool mounting hole for installation of the medical tool.

The holder supporting member may include a holder support rod shaped like a rod and having a first end coupled to the holder main body, a connecting plate formed at a second end of the holder support rod, and an arm connecting member connected to the connecting plate.

The support member installation groove may include a bolt insertion hole including a bolt head insertion groove and a thread insertion groove.

The holder connecting member may include a bolt inserted into the bolt insertion hole, and a stop pin inserted between the holder support rod and the holder main body.

Meanwhile, the tool installation groove may include an elastic pressuring unit to apply an elastic force to the medical tool inserted therein.

The holder may further include: an impact-reducing device installed in the holder main body to absorb and buffer an impact force applied to the holder main body, and an impact-reducing device insertion portion formed in a second end portion of the tool mounting hole to install the impact-reducing device.

Preferably, the impact-reducing device may include: an impact-reducing device main body formed with a tool insertion hole in which a tool shaft of the medical tool is inserted; an impact absorbing member placed in the impact-reducing device main body and absorbing impact applied to the medical tool; and a separation preventing member installed in the impact-reducing device main body to prevent separation of the impact absorbing member.

Meanwhile, the holder may further include a tool connecting means configured to restrain the medical tool inserted in the tool installation groove Preferably, the tool connecting means may include: a connecting hole formed penetrating the holder main body to communicate with the inside of the tool installation groove; a tool connecting member inserted through the connecting hole; and a locking portion formed in the medical tool so that the tool connecting member can be inserted therein and locked thereto.

The medical tool may include a straight or curved impactor including the tool shaft and used in hip joint surgery, and the impactor may include an impactor holding member which is coupled to the tool installation groove to movably support the straight impactor or the curved impactor, movably inserts the tool shaft therein, and is formed with a locking portion, and a stopper which restricts the movement of the tool shaft.

In this case, the stopper may be configured as a stop pin formed in the tool shaft corresponding to a portion for connection with the impactor holding member.

the impactor holding member may include a cylindrical body inserted into the tool shaft and formed with the locking portion, and a movement elongated hole formed in the longitudinal direction of the cylindrical body and limiting the movement of the stop pin.

The locking portion may include an introducing groove recessed in an inner end portion of the cylindrical body, and a locking groove extending curvedly from the introducing groove.

Meanwhile, the medical tool may be provided with the tool shaft, and includes a straight or curved reamer used in hip joint surgery, the straight or curved reamer may include a reamer frame having a hollow column structure to be externally put and installed on the tool shaft, and the reamer frame may include the locking portion formed in a portion to be inserted in the tool installation groove, the locking portion including an introducing groove recessed in an inner end portion of the reamer frame, and a locking groove extending curvedly from the introducing groove.

Advantageous Effects

A holder for medical tools according to the disclosure has effects on being conveniently usable with various medical tools interchangeably mounted thereto, such as an impactor, a reamer and a marker, in spite of a concise and simple structure where a tool support means and a tool connecting means are provided in a holder main body shaped like a hollow column, and has advantages of ensuring operational stability, improving durability, and enabling safe surgery because there is no cause for failure due to the concise and simple structure.

In addition, the holder for medical tools according to the disclosure prevents a medical tool or peripheral devices from being deformed or damaged because an impact absorbing member absorbs and buffers an impact force when installed on a tool shaft of the medical tool to which the impact force is applied.

DESCRIPTION OF DRAWINGS

FIGS. 8A to 8H are views for illustrating an impact-reducing device in a holder for medical tools according to an embodiment of the disclosure, in which FIG. 8A is an exploded perspective view, FIG. 8B is a perspective view for illustrating an internal structure, FIG. 8C is a lateral view, FIG. 8D is an enlarged view of an elastic member, FIG. 8E is an enlarged view of a separation preventing member, FIG. 8F is a partially cutaway perspective view, and FIGS. 8G and 8H are views for illustrating use states of the impact-reducing device, in which FIG. 8G is a partially enlarged view for illustrating a state that a hammer normally strikes a striking portion of the impactor, and FIG. 8H is a partially enlarged view for illustrating a state that the hammer misses the striking portion of the impactor.

BEST MODE

Below, exemplary embodiments of the disclosure will be described in detail with reference to FIGS. 1 to 11, in which like numerals refer to like components throughout FIGS. 1 to 11.

Meanwhile, detailed descriptions about components and their operations and effects, which are easily understood by a person having ordinary knowledge in the art from general technology, in the accompanying drawings will be simplified or omitted. In addition, the disclosure is characterized in a holder for medical tools, and thus illustration and description will be made focusing on related parts while simplifying or omitting the other parts. Although the holder for medical tools according to an embodiment of the disclosure may be used for holding various medical tools applied to surgical operations or the like, the following descriptions will be based on an example that the holder is applied to a reamer and an impactor used in artificial hip joint surgery.

Figure 1:
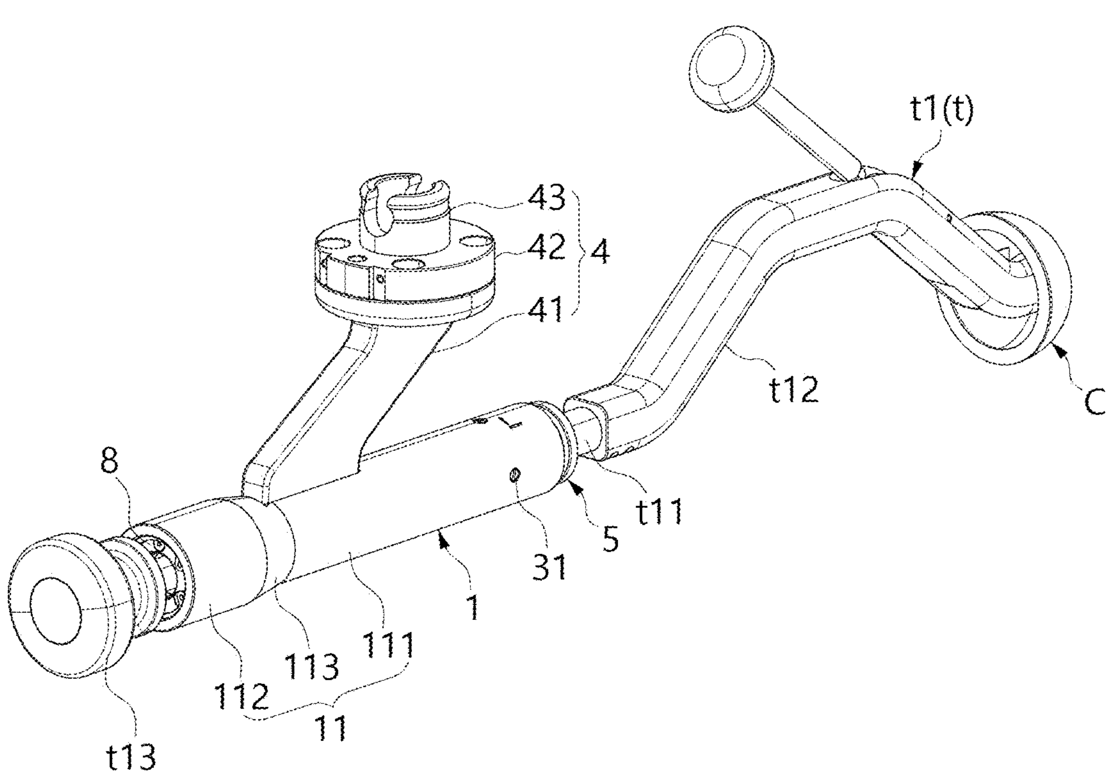
FIG. 1 is a perspective view of a holder for medical tools according to an embodiment of the disclosure.
Figure 2:
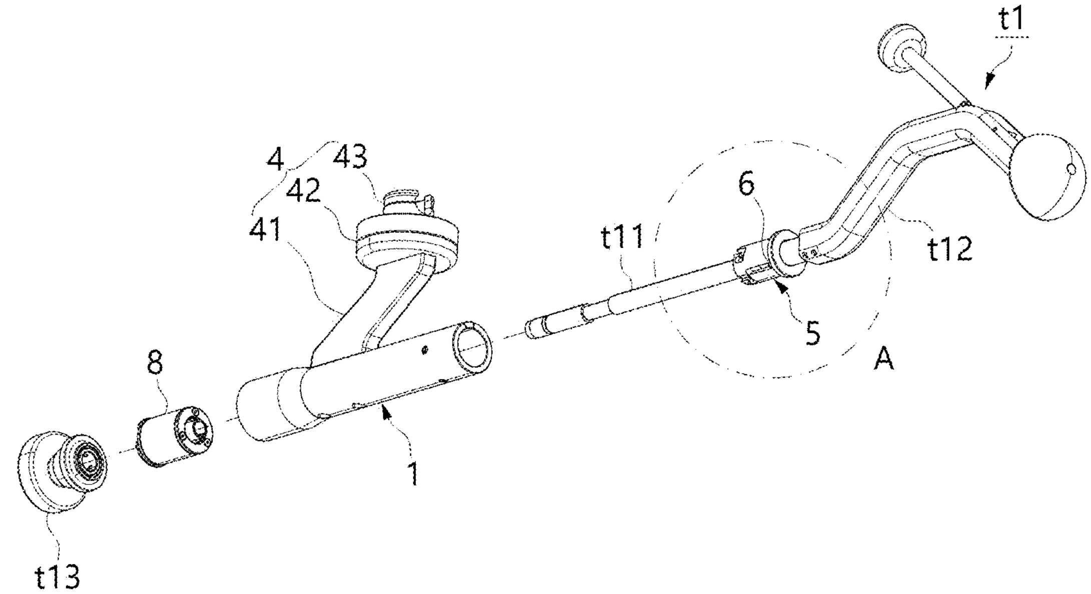
FIG. 2 is a partially exploded perspective view of a holder for medical tools according to an embodiment of the disclosure.
Figure 3:
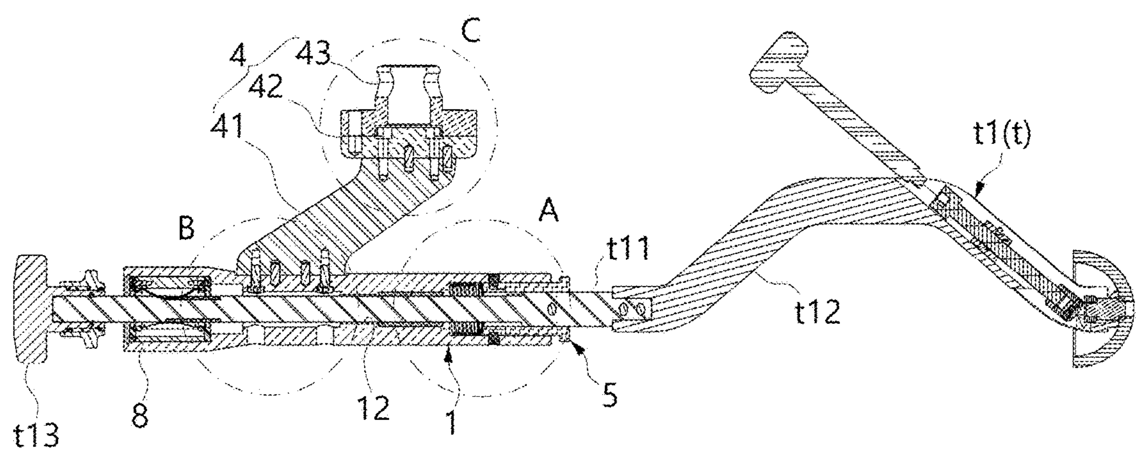
FIG. 3 is a cross-sectional view of a holder for medical tools according to an embodiment of the disclosure.
Figure 4A:
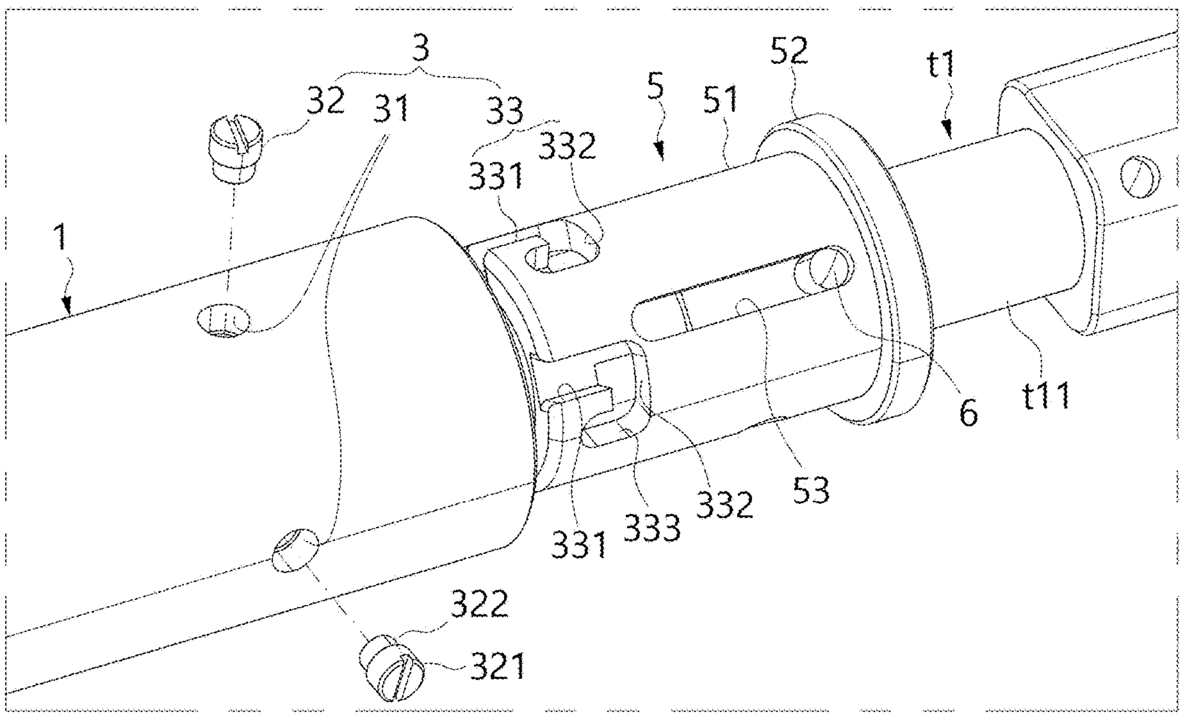
FIG. 4A is a perspective view of a section A in FIG. 2.
Figure 4B:
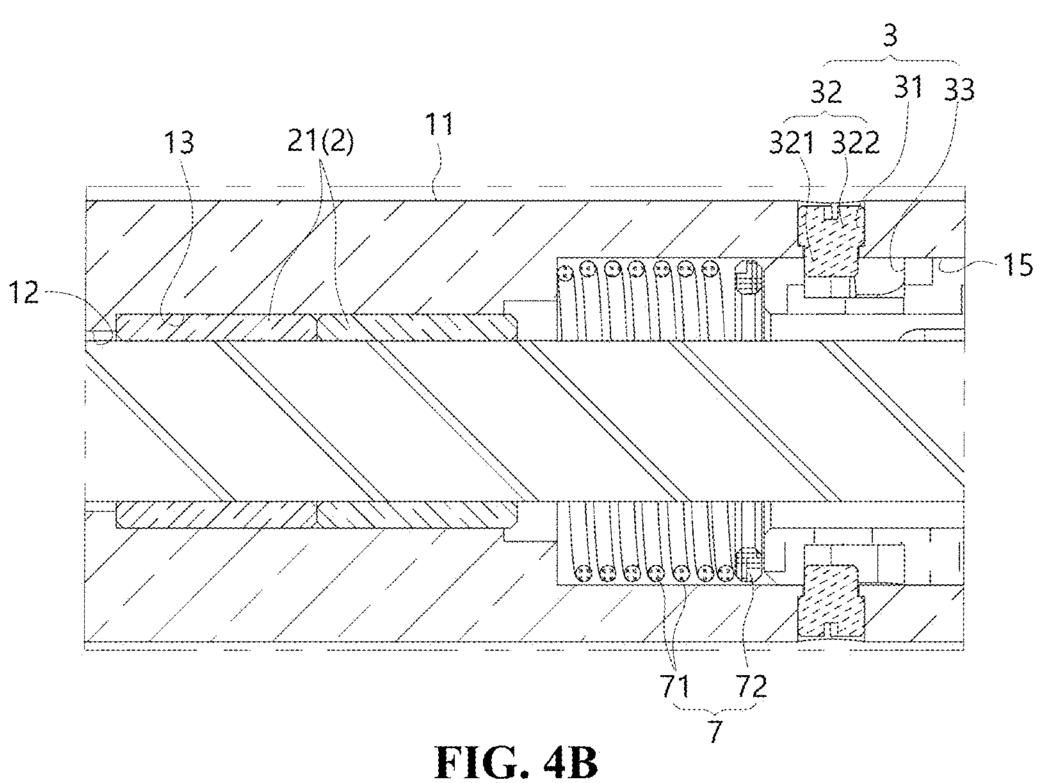
FIG. 4B is an enlarged view of the section A in FIG. 3.
Figure 4C:
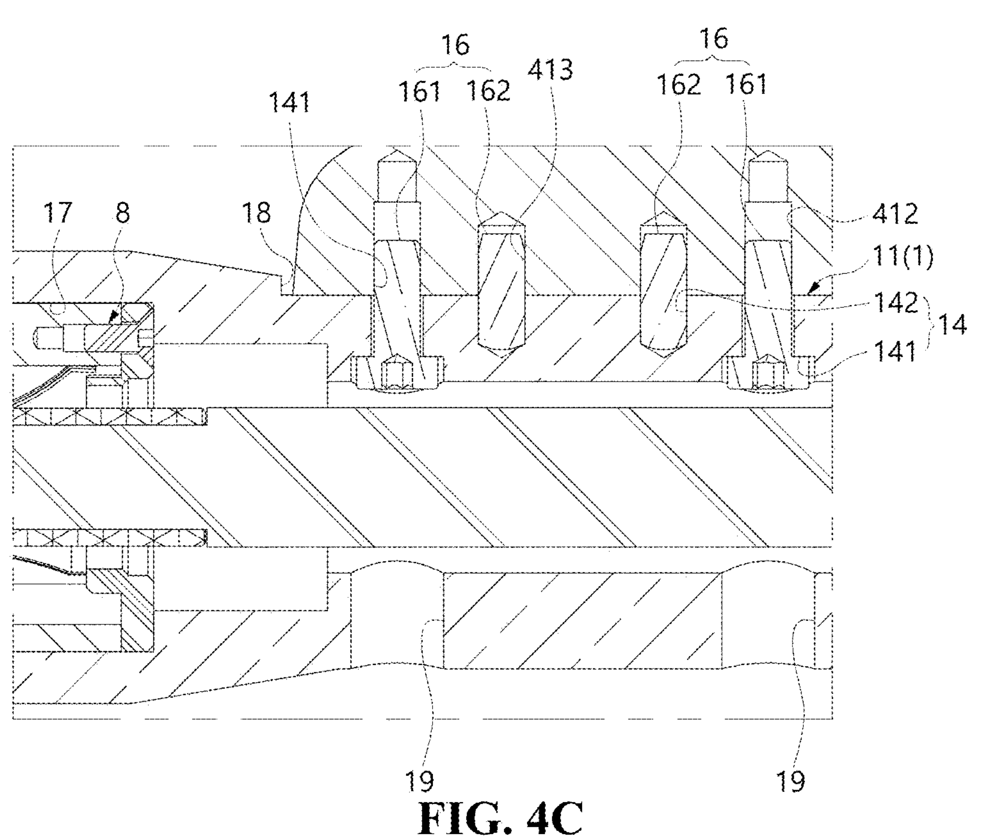
FIG. 4C is an enlarged view of a section B in FIG. 3.
Figure 4D:
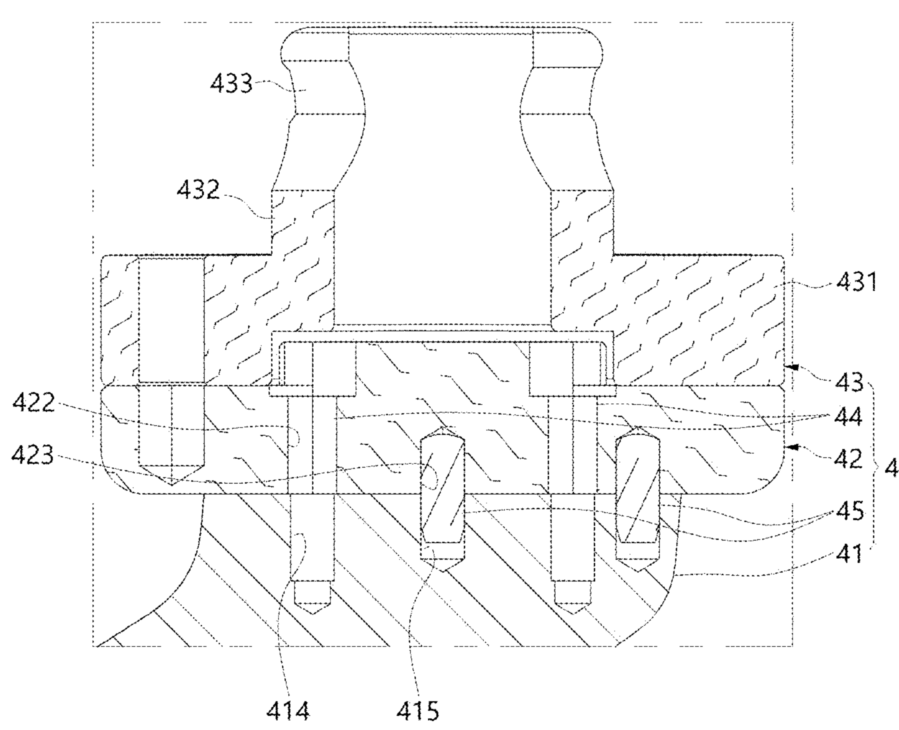
FIG. 4D is an enlarged view of a section C in FIG. 3.
Figure 5:
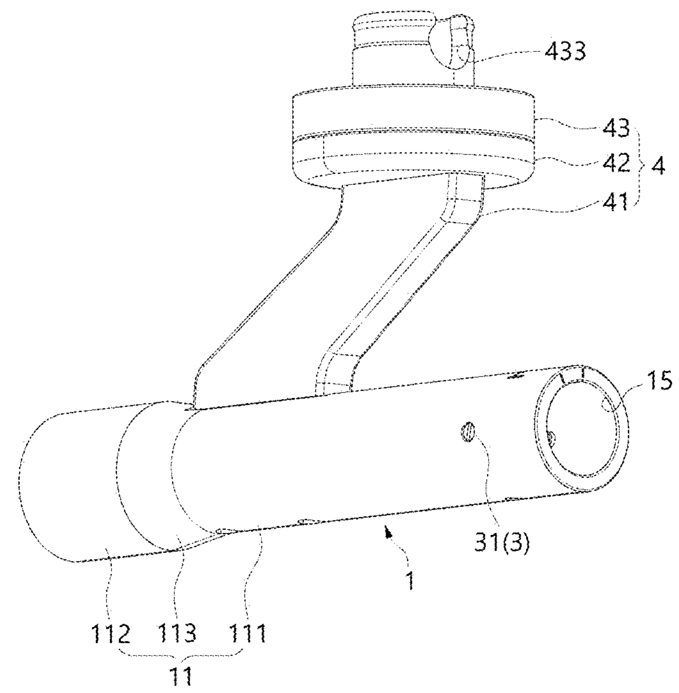
FIG. 5 is a perspective view of a holder main body in a holder for medical tools according to an embodiment of the disclosure.
Figure 6:
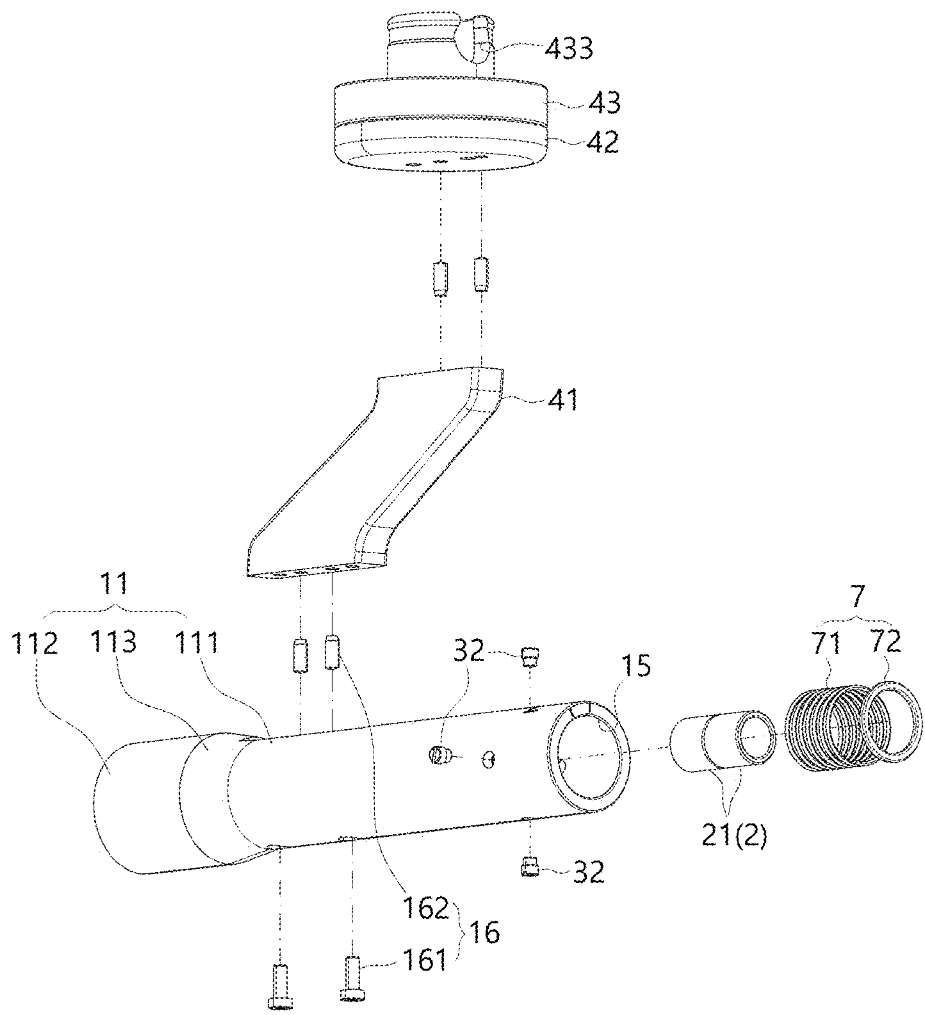
FIG. 6 is an exploded perspective view of a holder main body in a holder for medical tools according to an embodiment of the disclosure.
Figure 7A:
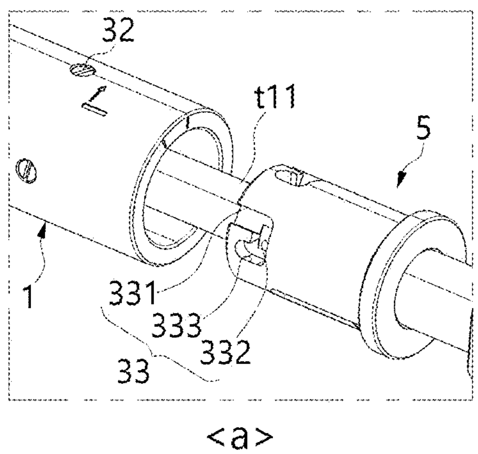
FIG. 7A is a view for illustrating a process of mounting a medical tool to a holder for medical tools according to an embodiment of the disclosure.
Figure 7A:
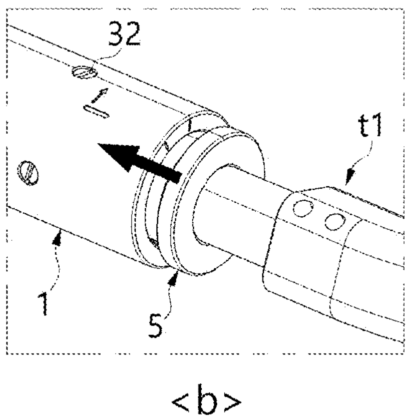
Figure 7A:
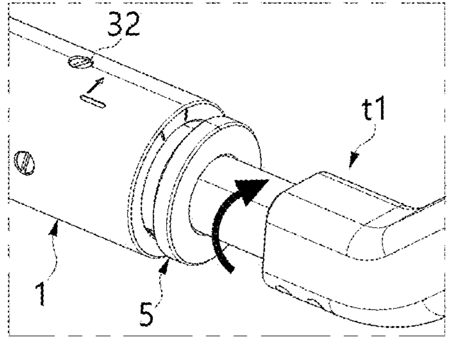
Figure 7B:
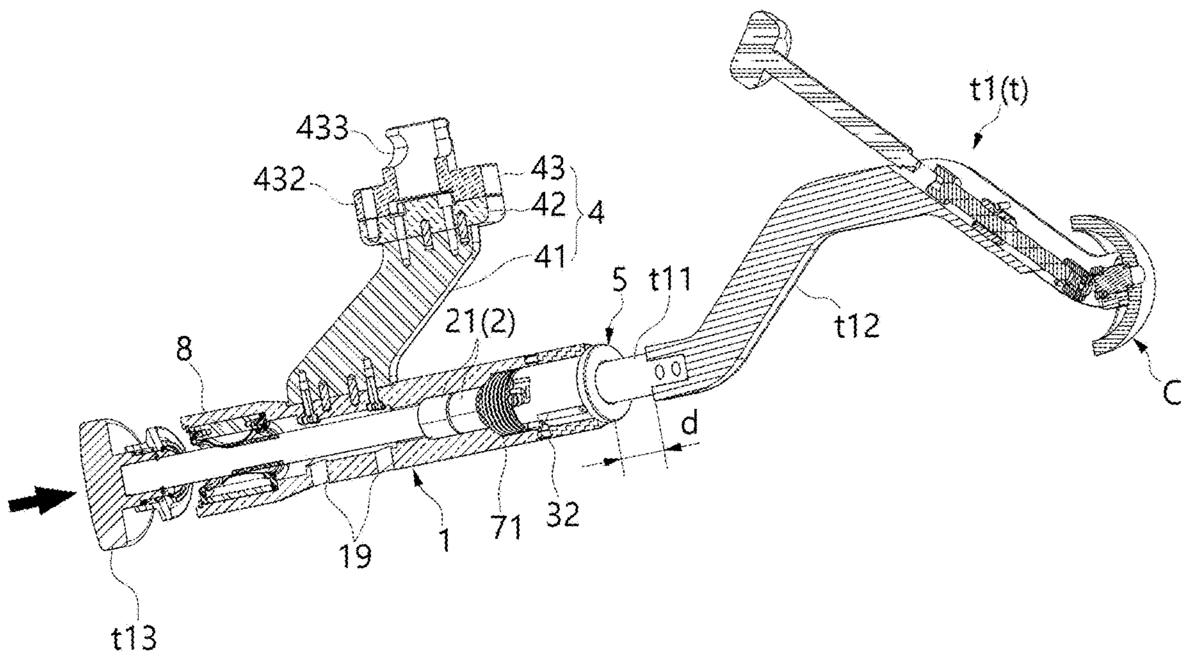
FIG. 7B is a view for illustrating a use state of an impactor installed as a medical tool in a holder for medical tools according to an embodiment of the disclosure.

FIG. 1 is a perspective view of a holder for medical tools according to an embodiment of the disclosure, FIG. 2 is a partially exploded perspective view of a holder for medical tools according to an embodiment of the disclosure, FIG. 3 is a cross-sectional view of a holder for medical tools according to an embodiment of the disclosure, FIG. 4A is a perspective view of a section A in FIG. 2, FIG. 4B is an enlarged view of the section A in FIG. 3, FIG. 4C is an enlarged view of a section B in FIG. 3, FIG. 4D is an enlarged view of a section C in FIG. 3, FIG. 5 is a perspective view of a holder main body in a holder for medical tools according to an embodiment of the disclosure, and FIG. 6 is an exploded perspective view of a holder main body in a holder for medical tools according to an embodiment of the disclosure. FIG. 7A is a view for illustrating a process of mounting a medical tool to a holder for medical tools according to an embodiment of the disclosure, and FIG. 7B is a view for illustrating a use state of an impactor installed as a medical tool in a holder for medical tools according to an embodiment of the disclosure.

Referring to FIGS. 1 to 7B, a holder for medical tools according to an embodiment of the disclosure includes a medical tool t, a holder main body 1, a tool supporting means 2, a tool connecting means 3, and a holder supporting member 4, and is characterized in having a concise and simple structure, satisfying operational stability and durability, and being usable with various medical tools interchangeably mounted thereto.

The medical tool t is not particularly limited as long as it is a medical tool having a tool shaft t11, but will be described based on an example where an impactor t1 and a reamer t2 (to be described later) are provided. Besides, the medical tool t may be applied with a marker device having a tool shaft in addition to the impactor or the reamer. Further, the impactor t1 may be applied with a straight impactor, the outer appearance of which is shaped to have a straight structure, but will be described in this embodiment based on an example where a curved impactor, the outer appearance of which is shaped to have a curved structure, is applied.

The curved impactor is approximately shaped like a rod, and includes a straight tool shaft t11 to be inserted into the holder main body 1, a tool curved portion t12 extending toward a first side of the tool shaft, and a cap-shaped striking portion t13 installed at a second end of the tool shaft and receiving a striking force from the hammer during surgery.

The curved impactor is provided with an impactor holding member 5 movably inserted into the tool shaft t11, coupled to a tool installation groove 15 of the holder main body 1 (to be described later) and formed with a locking portion 33 (to be described later). In addition, considering that the curved impactor advances and retreats during surgery, the curved impactor is provided with a stopper 6 installed in the tool shaft t11 and restricting the movement of the impactor holding member 5.

As shown in FIG. 4A, the impactor holding member 5 includes a cylindrical body 51 inserted into the tool shaft t11 and formed with the locking portion 33 (to be described later), a stop ring 52 that protrudes outwards from the cylindrical body 51, and a pair of movement elongated holes 53 formed in the longitudinal direction of the cylindrical body 51 and having a substantially oval structure to limit the movement of the stopper 6.

The stopper 6 is provided as a stop pin shaped like a round bar, and installed to penetrate an outer diameter portion of the tool shaft t11 corresponding to a portion for connection with the impactor holding member 5.

Meanwhile, the holder main body 1 refers to a component that functions as a housing to hold the medical tool t, and has a structure where a tool mounting hole 12 is formed longitudinally inside a hollow column body 11 for the insertion of the medical tool.

The hollow column body 11 includes a holder body 111 shaped like a pipe, an impact-reducing device installation portion 112 formed with an impact-reducing device insertion portion 17 having an inner diameter such that an outer diameter portion of an impact-reducing device 8 can be forcibly fitted into a front portion of the holder body, and a reducing portion 113 having a reduced inner diameter to prevent the impact-reducing device 8 from being pushed rearward even when an external force is applied thereto.

The tool mounting hole 12 includes a guide member installation groove 13 formed on the inner circumferential surface thereof to seat a tool support guide member 21 thereon, a support member installation groove 14 formed in contact with the guide member installation groove 13 to install a holder connecting member 16 for the installation of the holder supporting member 4, and a tool installation groove 15 formed at one end of the tool mounting hole 12 for the insertion of the medical tool.

The support member installation groove 14 includes a bolt insertion hole 141 having a bolt head insertion groove and a thread insertion groove for the insertion of a bolt 161 (to be described later), and a pin insertion hole 142 recessed being adjacent to the bolt insertion hole 141.

The holder connecting member 16 includes the bolt 161 inserted into the bolt insertion hole 141, and a stop pin 162 inserted between a holder support rod 41 and the holder main body 1.

In addition, the holder main body 1 includes a bolt incoming hole 19 drilled in a downward direction so as to be coaxial with the bolt insertion hole 141 and allow the bolt 161 to be inserted therethrough when fastening the bolt 161, and a rod seating groove 18 recessed to seat the lower end of the holder support rod 41 thereon.

Meanwhile, the tool supporting means 2 refers to a component that supports the medical tool inserted into the holder main body 1, and includes the tool support guide member 21 that guides the movement of the tool shaft t11 while supporting the tool shaft t11.

The tool support guide member 21 is configured as a sliding support body having an outer circumferential surface which is coupled to the inner circumferential surface of the guide member installation groove 13 provided in the tool mounting hole 12, and an inner circumferential surface into which the tool shaft t11 is inserted. The sliding support body may be configured as a bearing, but in this embodiment, installed as a plurality of sliding bushings commonly referred to as oilless bushings.

Meanwhile, the holder supporting member 4 refers to a component having a first end connected to the holder main body 1 to perform a function of supporting the holder main body 1 and a second end installed on an arm, etc. of a medical robot.

The holder supporting member 4 includes a holder support rod 41 shaped like a rod and having a first end coupled to the holder main body 1, a connecting plate 42 formed at a second end of the holder support rod 41, and an arm connecting member 43 connected to the connecting plate 42.

The holder support rod 41 refers to a member shaped like a rod and formed to be inclined, and has a lower end seated on the rod seating groove 18 of the holder main body 1 and coupled by the bolt 161 and the stop pin 162 described above, in which a fastening hole 412 and a pin insertion hole 413 are formed at positions corresponding to the bolt insertion hole 141 and the pin insertion hole 142 described above.

The connecting plate 42 may be formed integrally with the holder support rod 41, but is formed with a bolt fastening hole 422 and a pin insertion hole 423 so as to be fastened by a bolt 44 and a stop pin 45, thereby coupling with the holder support rod 41 as the bolt 44 and the stop pin 45 are inserted and fastened into a bolt fastening hole 414 and a pin insertion hole 415 corresponding to the bolt fastening hole 422 and the pin insertion hole 423 and formed in an upper portion of the holder support rod 41.

The arm connecting member 43 is configured as a clamp member that is connected to a robot-side clamping member (not shown) mounted to an opposing robot arm (not shown), in which the clamp member includes a disc-shaped clamp body 431 formed with a plurality of fastening holes, and a clamp protrusion 432 formed with a locking hole 433 into which a clamping shaft of the robot-side clamping member (not shown) is inserted or coupled.

Meanwhile, the tool connecting means 3 refers to a component for restraining the medical tool t inserted in the tool installation groove 15, and may be configured without specific limitations as long as the medical tool can be connected thereto and disconnected therefrom. However, in this embodiment, the tool connecting means 3 is characterized in allowing various medical tools to be interchangeably mounted thereto and released therefrom despite a concise and simple structure.

As shown in FIG. 4A, the tool connecting means 3 includes a plurality of connecting holes 31 formed around the holder main body 1 so as to communicate with the inside of the tool installation groove 15, a tool connecting member 32 inserted through the connecting hole 31, and a locking portion 33 formed in the medical tool t so that the tool connecting member 32 can be inserted therein and locked thereto.

The tool connecting member 32 includes a screw portion 321 fastened to the connecting hole 31, and a locking protrusion 322 formed at an end portion of the screw portion 321 and inserted into the locking portion 33.

The locking portion 33 is formed in the impactor holding member 5, and includes an introducing groove 331 recessed in an inner end portion of the cylindrical body 51, and a locking groove 332 extending from the introducing groove 331 and curved in a roughly 'L'-shape.

The process of mounting the medical tool t using the foregoing tool connecting means 3 will be briefly described with reference to FIGS. 7A and 7B. As shown in <a> of FIG. 7A, the locking protrusion 322 of the tool connecting member 32 is aligned with the introducing groove 331. The medical tool t1 is pressed to enter the introducing groove 331 as shown in <b> of FIG. 7A, and then rotated at an angle of approximately 30° along the locking groove 332 as shown in <c> of FIG. 7A. As a result, the medical tool t1 is inserted in a recessed end portion 333 of the locking groove 332 by the elastic force of an elastic pressing unit 7, so that the medical tool t1 can be stably locked not to be separated.

Meanwhile, the tool installation groove 15 is provided with the elastic pressuring unit 7 to apply an elastic force to stably lock the medical tool inserted therein.

The elastic pressing unit 7 includes a compression coil spring 71 providing the elastic force to the medical tool t introduced into the tool installation groove 15, and a pressurizing ring 72 pressing the medical tool by the elastic force applied from the compression coil spring 71.

Figure 8A:
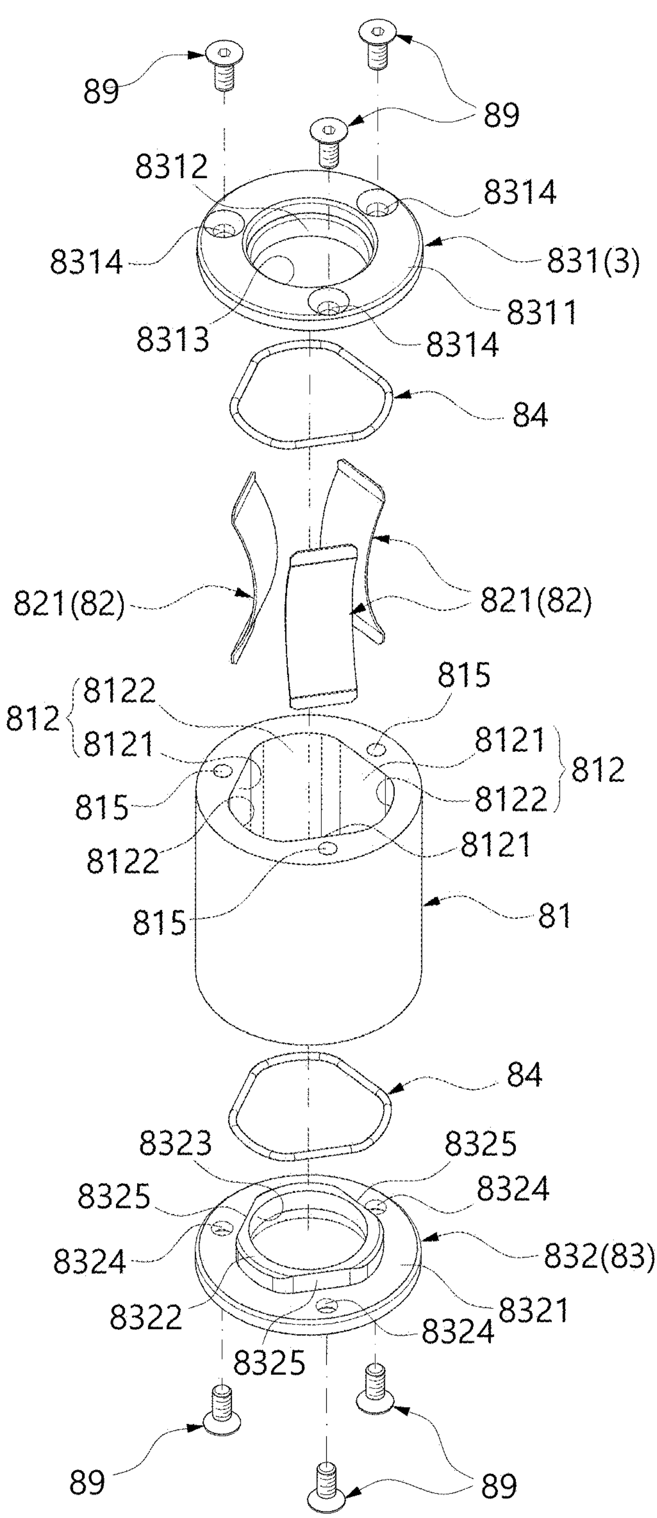
Figure 8B:
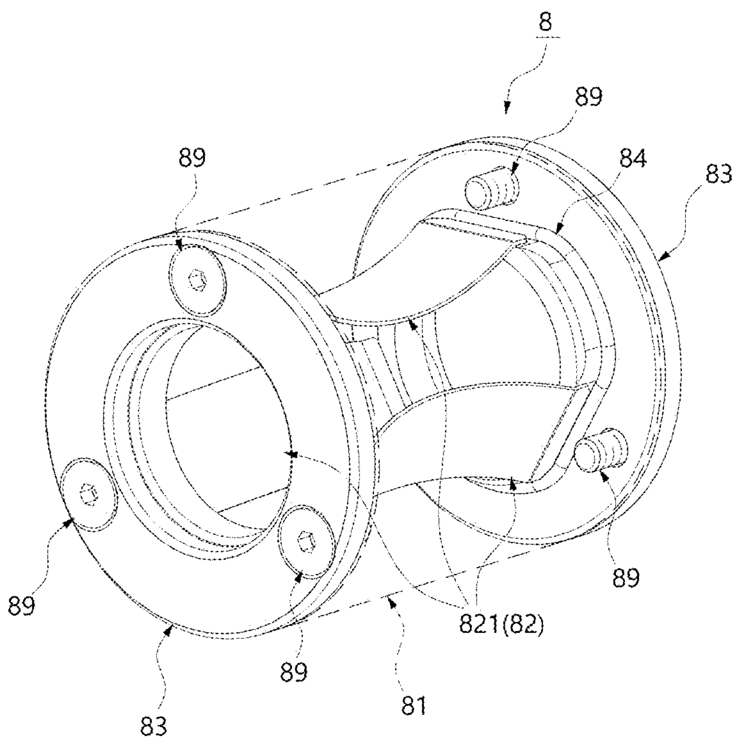
Figure 8C:
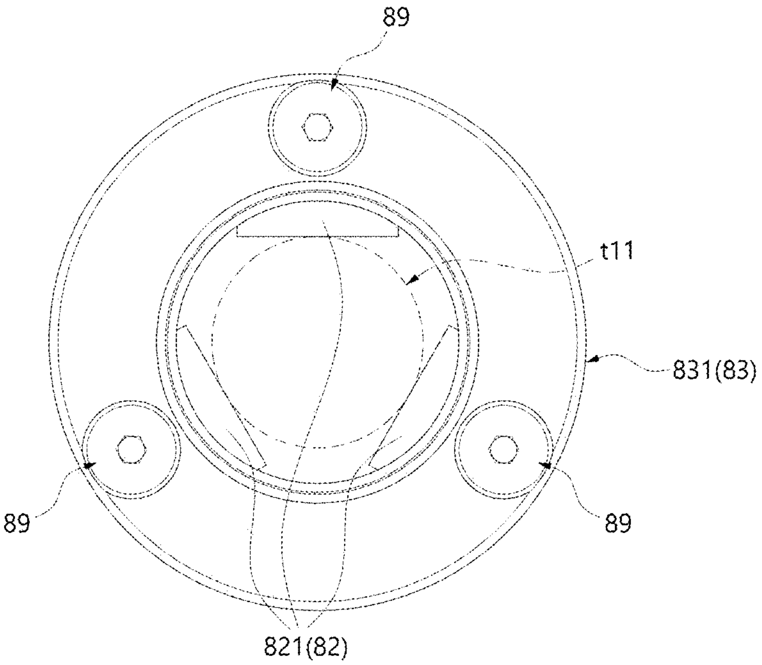
Figure 8D:
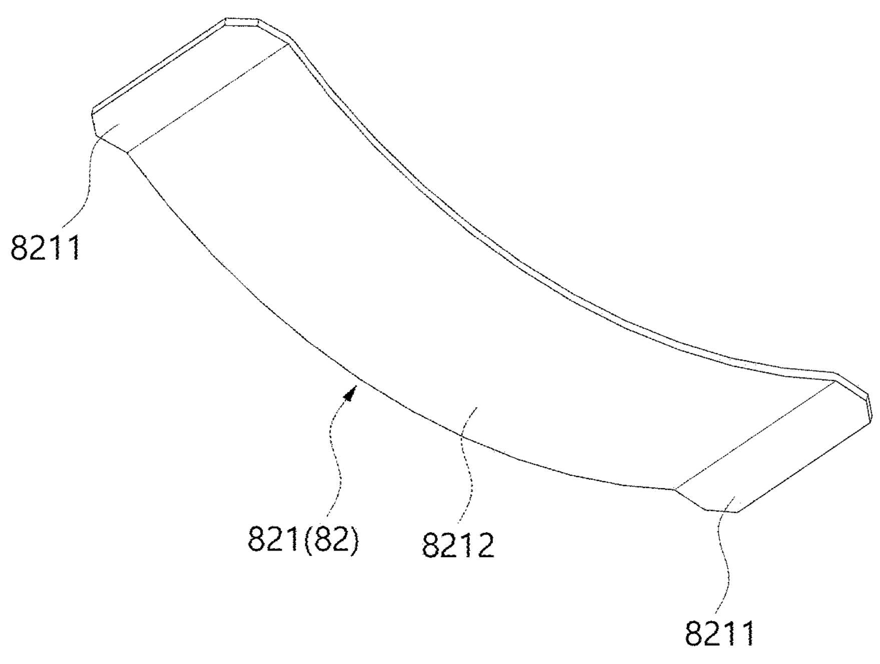
Figure 8E:
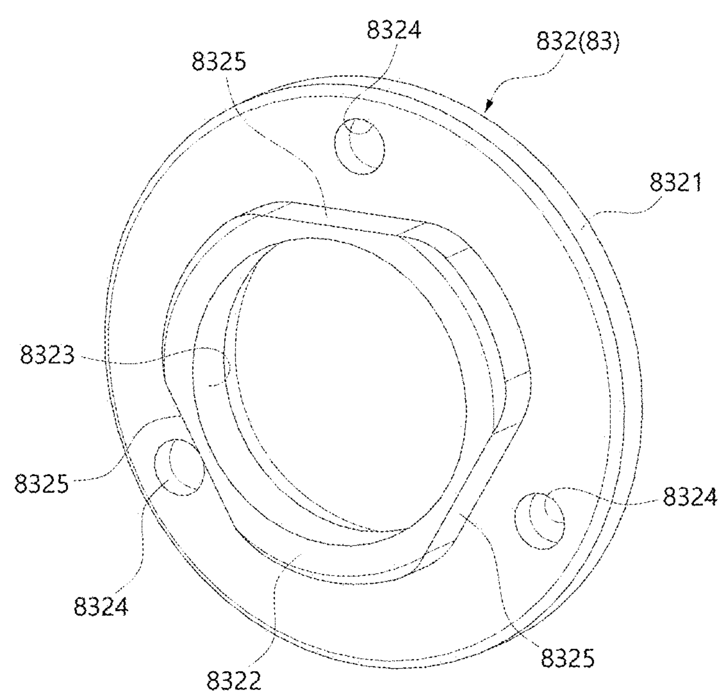
Figure 8F:
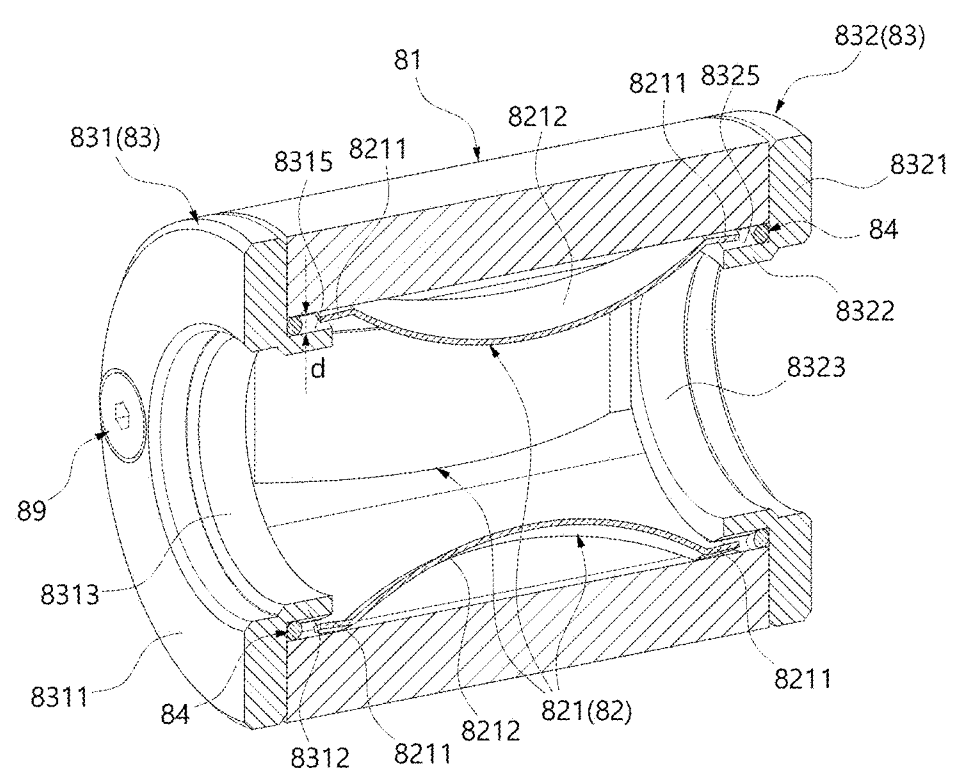
Figure 8G:
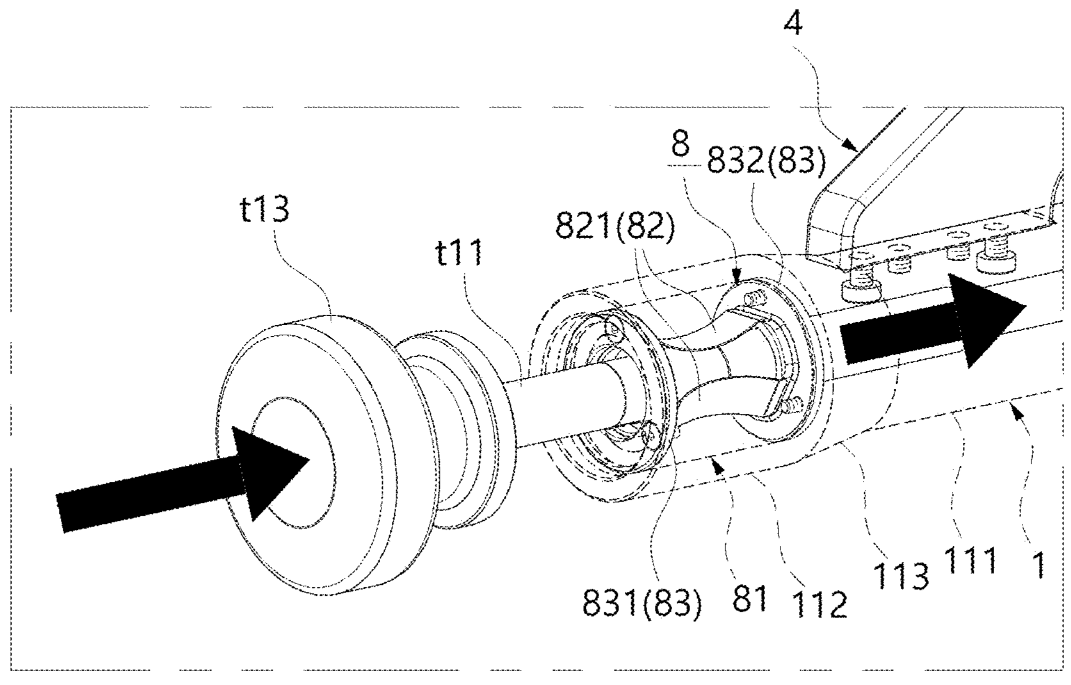
Figure 8H:
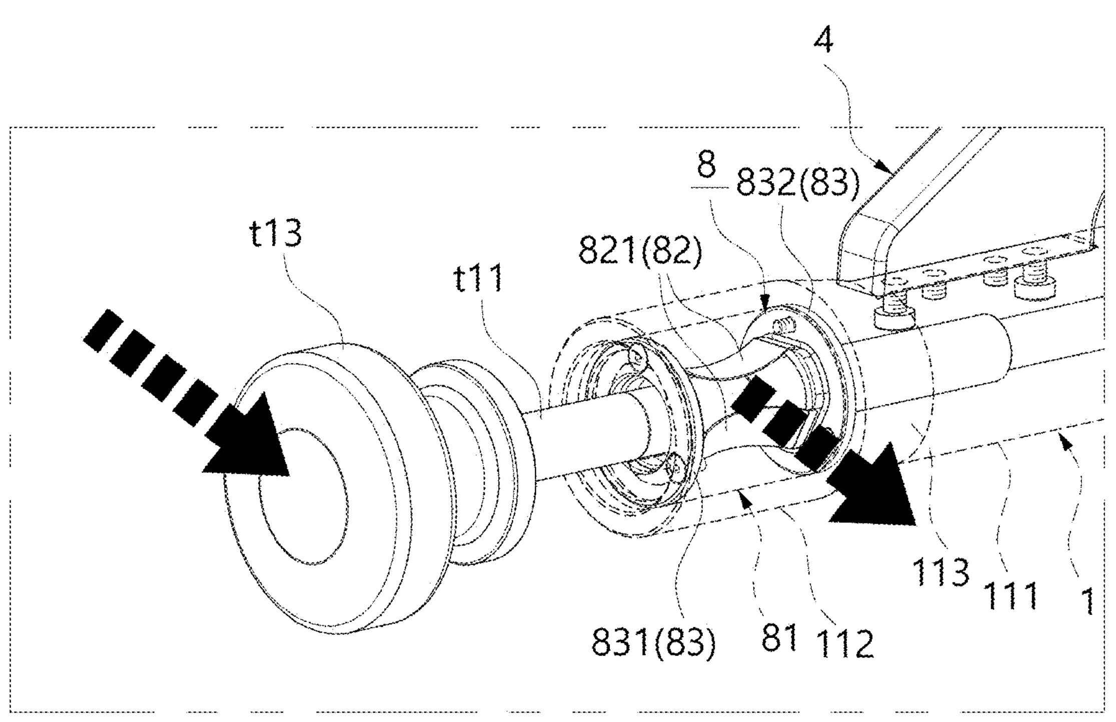

FIGS. 8A to 8H are views for illustrating an impact-reducing device in a holder for medical tools according to an embodiment of the disclosure, in which FIG. 8A is an exploded perspective view, FIG. 8B is a perspective view for illustrating an internal structure, FIG. 8C is a lateral view, FIG. 8D is an enlarged view of an elastic member, FIG. 8E is an enlarged view of a separation preventing member, and FIG. 8F is a partially cutaway perspective view. FIGS. 8G and 8H are views for illustrating use states of the impact-reducing device, in which FIG. 8G is a partially enlarged view for illustrating a state that a hammer normally strikes a striking portion of the impactor, and FIG. 8H is a partially enlarged view for illustrating a state that the hammer misses the striking portion of the impactor.

Referring to FIGS. 8A to 8H, a holder for medical tools according to an embodiment of the disclosure includes a holder main body 1 formed with the impact-reducing device insertion portion 17 formed at the second end portion of the toll mounting hole 12, and the impact-reducing device 8 installed in the holder main body 1 to absorb and buffer an impact force applied to the holder main body 1 through the impact-reducing device insertion portion 17.

The impact-reducing device 8 includes an impact-reducing device main body 81, an impact absorbing member 82, a separation preventing member 83 and a sealing member 84, to absorb and buffer abnormal impact even though the abnormal impact is applied to the medical tool, thereby preventing damage to the holder main body 1, the medical tool t, etc. or an adverse effect on surgery.

The impact-reducing device main body 81 refers to a component installed in the holder main body, in which an impactor t1 or the like medical tool is inserted, as a part of functioning as a basic framework, and is formed with a tool insertion hole 812 into which a tool shaft t11 of the medical tool is inserted.

The impact-reducing device main body 81 is approximately shaped like a cylinder and is formed with the tool insertion hole 812 into which the tool shaft t11 of the medical tool such as the impactor t1 is inserted.

The tool insertion hole 812 is shaped corresponding to first and second separation preventing protrusions 8312 and 8322 (to be described later) so that the first and second separation preventing protrusions 8312 and 8322 can be inserted therein, but has an inner diameter larger than outer diameters of the first and second separation preventing protrusions 8312 and 8322 so as to form a gap d for the insertion of a sealing member 84 and the insertion of an elastic member 821 between the tool insertion hole 812 and the first and second separation preventing protrusions 8312 and 8322. For example, the tool insertion hole 812 is formed as a hole shaped like an approximately triangular prism that has three hole-flat portions 8121 for inserting three plate springs, and three rounded-edge portions 8122 for connecting the hole-flat portions 8121.

In addition, the impact-reducing device main body 81 is formed with fastening holes 815 on the front and rear surfaces thereof being in contact with the tool insertion hole 812 so as to couple with fastening screws 89.

Meanwhile, the impact absorbing member 82 refers to a component that is placed in the impact-reducing device main body 81 and absorbs impact applied to the medical tool, and includes an elastic member 821 embedded in the impact-reducing device main body 81 to absorb the impact applied to the tool shaft t11.

The elastic member 821 may be formed to have various shapes and structures without specific limitations as long as it can absorb and buffer an oblique impact force transmitted from the tool shaft t11. Considering that the tool shaft t11 in this embodiment is shaped like a round bar, the elastic member 821 includes a plurality of plate springs that are formed convexly to come into contact with the outer surface of the tool shaft t11 and absorb the impact force.

Preferably, the plate spring is structured to have fitting portions 8211 formed at both ends thereof, and a convex portion 8212 formed between the fitting portions 8211 and protruding convexly toward the center of the tool insertion hole 812, which may be formed by bending and folding a rectangular plate material. In addition, the plate spring may be manufactured by selecting any material as long as it has elasticity without specific limitations. According to this embodiment, the plate spring is manufactured using a thin metal plate of stainless steel excellent in hygiene and durability.

Meanwhile, the separation preventing member 83 refers to a component installed in the impact-reducing device main body 81 to prevent the separation of the impact absorbing member 82, and includes a first separation preventing flange 831 and a second separation preventing flange 832 connected to a first end and a second end, i.e., both ends of the impact-reducing device main body 81.

The first separation preventing flange 831 includes a first connecting portion 8311 connected to the first end of the impact-reducing device main body 81 and formed with a through hole 8313 communicating with the tool insertion hole 812, and a first separation preventing protrusion 8312 protruding from the inner surface of the first connecting portion 8311 and supporting the first end of the plate spring not to be separated.

In addition, the first connecting portion 8311 is formed with the through hole 8313 formed in the center of a body approximately shaped like a disc, and a plurality of fastening holes 8314 equiangularly drilled for coupling with the impact-reducing device main body 81.

The second separation preventing flange 832 includes a second connecting portion 8321 connected to the second end of the impact-reducing device main body 81 and formed with a through hole 8323 communicating with the tool insertion hole 812 formed in the center of the body approximately shaped like a disc, and a second separation preventing protrusion 8322 protruding from the inner surface of the second connecting portion 8321 and supporting the second end of the plate spring not to be separated.

Like the first connecting portion 8311, the second connecting portion 8321 has a structure in which the through hole 8323 and the plurality of fastening holes 8324 are formed in a disc-shaped body.

The first and second separation preventing protrusions 8312 and 8322 protrude along the peripheries of the through holes 8313 and 8323 so as to provide the gap d into which the fitting portion 8211 is inserted and accommodated while the first and second separation preventing flanges 831 and 832 are coupled to the impact-reducing device main body 81.

In particular, the first and second separation preventing protrusions 8312 and 8322 are characterized in including guide flat portions 8315 and 8325 having a flat structure to guide the movement of the fitting portions when the plate spring is compressed and stretched.

The sealing member 84 refers to a component that maintains the sealing of a connection area between the separation preventing member 83 and the impact-reducing device main body 81, and is provided as a sealing ring, i.e., a so-called O-ring.

Below, another application example of the holder for medical tools according to an embodiment of the disclosure will be described, in which detailed descriptions about components similar to those shown in the foregoing embodiments are omitted and descriptions are made focusing on different components.

Figure 9:
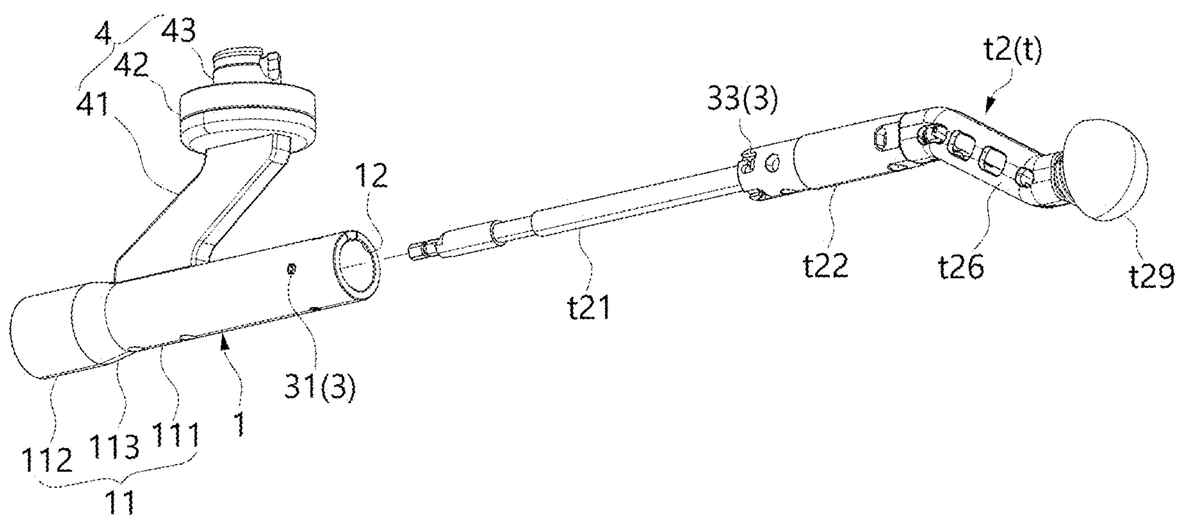
FIG. 9 is a perspective view showing another application example of a holder for medical tools according to an embodiment of the disclosure.
Figure 10:
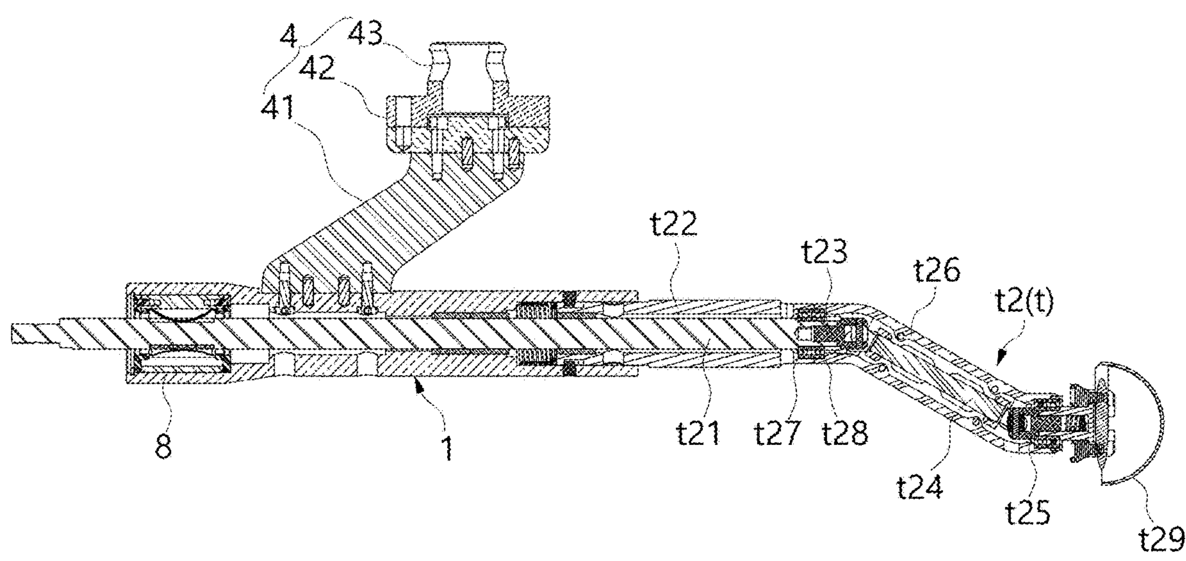
FIG. 10 is a cross-sectional view showing another application example of a holder for medical tools according to an embodiment of the disclosure.
Figure 11:
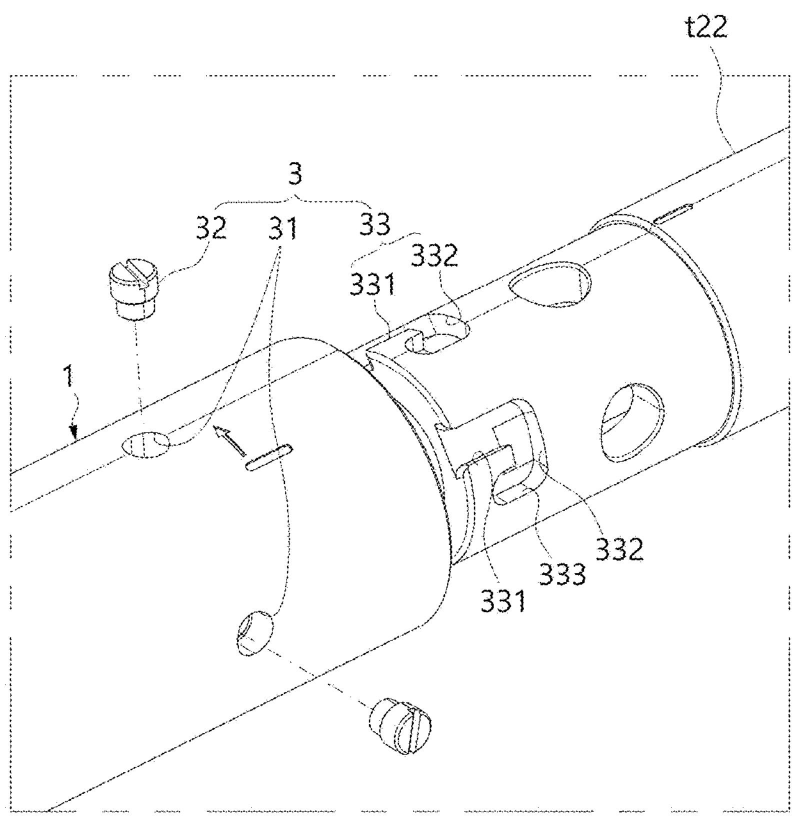
FIG. 11 is a partially enlarged exploded-perspective view another application example of a holder for medical tools according to an embodiment of the disclosure.

FIG. 9 is a perspective view showing another application example of a holder for medical tools according to an embodiment of the disclosure, FIG. 10 is a cross-sectional view showing another application example of a holder for medical tools according to an embodiment of the disclosure, and FIG. 11 is a partially enlarged exploded-perspective view another application example of a holder for medical tools according to an embodiment of the disclosure Referring to FIGS. 9 to 11, the holder for the medical tools according to this application example of the disclosure includes the medical tool t, the holder main body 1, the tool supporting means 2, the tool connecting means 3, the holder supporting member 4, and the elastic pressing unit 7 as described above, in which the medical tool t is not the foregoing impactor t1 but a reamer t2.

The reamer t2 may be applied with a straight reamer, the outer appearance of which is shaped to have a straight structure, but will be described in this application example based on an example where a curved reamer (called an offset reamer), the outer appearance of which is shaped to have a curved structure.

The curved reamer t2 is roughly shaped like a rod, and includes a tool shaft t21 having a straight structure to be inserted in the holder main body 1, a reamer frame t22 having a hollow column structure to be externally put and installed on the tool shaft, a universal joint t23 having a first end connected to the rear end of the tool shaft t21, an offset shaft t24 to which a second end of the universal joint t23 is connected, a cup locking member t25 having a first end connected to the offset shaft t24, and a reamer basket-cup t29 connected to a second end of the cup locking member t25 and performing a cutting operation.

In addition, the curved reamer t2 is provided with an offset frame t26 installed to be externally overlaid on the universal joint t23, the offset shaft t24 and the cup locking member t25, and is guided to rotate by a first axial support bearing t27 installed between the outer circumferential rear-end surface of the tool shaft t21 and the inner circumferential front-end surface of the reamer frame t22, and a second axial support bearing t28 installed between the outer circumferential rear-end surface of the tool shaft t21 and the inner circumferential front-end surface of the offset frame t26.

The tool connecting means 3 includes a plurality of connecting holes 31 formed around the holder main body 1 so as to communicate with the inside of the tool installation groove 15, a tool connecting member 32 inserted through the connecting hole 31, and a locking portion 33 formed in the medical tool so that the tool connecting member 32 can be inserted therein and locked thereto, in which the locking portion 33 is formed in the reamer frame t22.

The locking portion 33 is formed at the front-end portion of the reamer frame t22 inserted into the tool installation groove 15, and includes an introducing groove 331 inserted into the inner end portion of the reamer frame t22 and a locking groove 332 extending curvedly from the introducing groove 331.

As shown in FIGS. 10 to 12, the holder for the medical tools according to this application example of the disclosure does not include the foregoing impactor holding member 5 and the foregoing stopper 5 because the reamer configured as the medical tool t requires only the rotating operation without the advancing and retreating operations.

Further, the reamer is not subject to an impact force during the surgical process and thus does not necessarily require the impact-reducing device 8. However, it is preferable that the impact-reducing device 8 be installed in the holder main body 1 because the reamer is likely to absorb an unexpected impact force applied from the outside and elastically supports the tool shaft t21 in front of the holder main body 1.

Below, the operations of a holder for medical tools according to an embodiment of the disclosure will be briefly described.

The procedure for performing artificial hip joint surgery using the foregoing holder for medical tools according to the disclosure is usually performed by preprocessing the acetabulum of the hip joint by cutting, etc. using the reamer, inserting the artificial acetabulum-cup c, pressing and fixing the preprocessed acetabulum using the impactor, and then connecting an artificial femoral head.

To this end, the holder supporting member 4 of the holder main body 1 is first coupled to an arm (not shown) of an artificial joint surgery robot, and the curved reamer t2 is mounted as the medical tool.

Referring to FIG. 11, the curved reamer t2 is mounted in such a way that the tool shaft t21 is inserted into the tool mounting hole 12 and fastened using the tool connecting means 3. Like the method of mounting the impactor t1 described above with reference to FIG. 7A, the curved reamer t2 is also mounted in such a manner that the locking protrusion 322 of the tool connecting member 32 is aligned with the introducing groove 331, the medical tool t2 is pressed to enter the introducing groove 331 and then rotated counterclockwise at an angle of approximately 30° along the locking groove 332 so that the medical tool t2 can be inserted in the recessed end portion 333 of the locking groove 332 by the elastic force of the elastic pressing unit 7 and thus be stably locked not to be separated.

When the curved reamer t2 is completely mounted in this way, a front portion of the tool shaft t21 is rotatably elastically supported by the impact absorbing member 82 of the impact-reducing device 8, an approximate central portion of the tool shaft t21 is rotatably supported by the tool support guide member 21, and a rear end portion of the tool shaft t21 is rotatably supported by the first shaft support bearing t27 and the second shaft support bearing t28. Therefore, when the rotational power of a driving motor (not shown) or the rotational power by a manual operation is transmitted to the tool shaft t21, the tool shaft t21 performs the rotational operation smoothly.

In this way, the rotational power transmitted to the tool shaft t21 is transmitted to the offset shaft t24 and the cup locking member t25 via the universal joint t23, and thus the reamer basket cup t29 cuts the acetabulum of the hip joint while rotating.

When the preprocessing such as the cutting, etc. is completed, the curved reamer t2 is separated in reverse order to the mounting operation. In other words, when the curved reamer t2 is pushed inward so that the locking protrusion 322 can come out of the recessed end 333 and then rotated clockwise at an angle of approximately 30° along the locking groove 332, the locking protrusion 322 is separated and unmounted outward along the introducing groove 331 by the elastic force of the elastic pressing unit 7.

Meanwhile, after the curved reamer t2 is separated as described above, the impactor t1 such as the curved impactor is mounted to the holder main body 1, thereby completing the surgery by pressing and fitting the artificial acetabulum-cup c, and connecting the artificial femoral head.

The impactor t1 is mounted in such a way that the tool shaft t11 is inserted into the tool mounting hole 12 and fastened using the tool connecting means 3. As shown in <a> of FIG. 7A, the locking protrusion 322 of the tool connecting member 32 is aligned with the introducing groove 331. The medical tool t1 is pressed to enter the introducing groove 331 as shown in <b> of FIG. 7A, and then rotated at an angle of approximately 30° along the locking groove 332 as shown in <c> of FIG. 7A. As a result, the medical tool t1 is inserted in the recessed end portion 333 of the locking groove 332 by the elastic force of the elastic pressing unit 7, so that the medical tool t1 can be stably locked not to be separated.

When the impactor t1 is mounted in this manner, the front portion of the tool shaft t11 is movably and elastically supported by the impact absorbing member 82 of the impact-reducing device 8, and the rear portion of the tool shaft t21 is movably supported by the tool support guide member 11.

Meanwhile, when the impactor t1 is completely mounted as shown in FIG. 1 and struck by the hammer (not shown), the tool shaft t1 may advance by 'd' as shown in FIG. 7B to perform the process of pressing and fitting the artificial acetabulum-cup into the acetabulum of the hip joint.

The surgical process of striking the impactor t1 may be performed in such a way that a user applies a striking force to the striking portion t13 by using the hammer as shown in FIG. 8G. When the striking direction of the hammer is aligned with the longitudinal direction, i.e., axial direction of the impactor, a surgical procedure is stably performed. On the other hand, when the striking direction of the hammer is misaligned with the axial direction of the impactor as shown in FIG. 8H to apply an impact force to the impactor in an oblique direction (i.e., wrong direction), the holder main body 1 and the impactor t1 may be deformed, damaged, and broken. In this case, the impact-reducing device 8 installed in the holder main body 1 functions to absorb the impact, thereby solving the foregoing problems.

In addition, the foregoing impact absorption function of the impact-reducing device 8 is performed in such a way that the mishit of the hammer applies a displacement force to the tool shaft t11 in an oblique direction due to the tool shaft t11 inserted in the tool insertion hole 812 as shown in FIG. 8H, and at the same time the convex portion 8212 becomes flat a little to absorb and buffer the impact force while the outer circumferential surface of the tool shaft t11 applies the displacement force to the elastic member 821.

The terms "include," "configure" and/or "have" specify the presence of stated components, unless there is a clearly different meaning in the disclosure, but do not preclude the presence thereof and should be construed to further include other components. Unless otherwise defined, all terms including technical or scientific terms used herein have the same meaning as commonly understood by those skilled in the art to which the disclosure pertains. General terms that are defined in a dictionary shall be construed to have meanings that are consistent in the context of the relevant art, and will not be interpreted as having an idealistic or excessively formalistic meaning unless clearly defined in the disclosure.

Although the configurations and operations of a holder for medical tools according to an embodiment of the disclosure has been described so far, it will be appreciated by those skilled in the art that modifications or substitutions can be made in all or part of the embodiments of the disclosure without departing from the technical spirit of the disclosure.

Accordingly, it will be understood that the scope of the disclosure falls into the appended claims and equivalents thereof.

INDUSTRIAL APPLICABILITY

The disclosure relates to a holder for medical tools, which has a concise and simple structure, satisfies operational stability and durability, and is usable interchangeably. The holder for medical tools may be mounted with an impactor, a reamer, and the like for surgical operations, but may also be used for various medical tools besides those for the surgical operations.

The invention claimed is:

1. A holder for medical tools, comprising:

a medical tool comprising a tool shaft;

a holder main body internally defined with a tool mounting hole to insert the medical tool therein;

a tool supporting means supporting the medical tool inserted in the holder main body; and a holder supporting member coupled to the holder main body, wherein the tool supporting means comprises a tool support guide member to guide movement of the tool shaft while supporting the tool shaft, and wherein the tool mounting hole comprises:

a guide member installation groove defined on an inner circumferential surface thereof to seat the tool support guide member thereon;

a support member installation groove defined in contact with the guide member installation groove to install a holder connecting member for installation of the holder supporting member; and a tool installation groove defined at one end portion of the tool mounting hole for installation of the medical tool.

2. The holder of claim 1, wherein the tool support guide member comprises a sliding support body that has an outer circumferential surface to couple with an inner circumferential surface of the tool mounting hole, and an inner circumferential surface into which the tool shaft is inserted.

3. The holder of claim 1, wherein the holder supporting member comprises a holder support rod shaped like a rod and having a first end coupled to the holder main body, a connecting plate disposed at a second end of the holder support rod, and an arm connecting member connected to the connecting plate, the support member installation groove comprises a bolt insertion hole comprising a bolt head insertion groove and a thread insertion groove, and the holder connecting member comprises a bolt inserted into the bolt insertion hole, and a stop pin inserted between the holder support rod and the holder main body.

4. The holder of claim 1, wherein the tool installation groove comprises an elastic pressuring unit to apply an elastic force to the medical tool inserted therein.

5. The holder of claim 1, further comprising:

an impact-reducing device installed in the holder main body to absorb and buffer an impact force applied to the holder main body, and an impact-reducing device insertion portion defined in a second end portion of the tool mounting hole to install the impact-reducing device.

6. The holder of claim 5, wherein the impact-reducing device comprises:

an impact-reducing device main body defined with a tool insertion hole in which the tool shaft of the medical tool is inserted;

an impact absorbing member disposed in the impact-reducing device main body and absorbing impact applied to the medical tool; and a separation preventing member installed in the impact-reducing device main body to prevent separation of the impact absorbing member.

7. The holder of claim 1, further comprising a tool connecting means configured to restrain the medical tool inserted in the tool installation groove.

8. The holder of claim 7, wherein the tool connecting means comprises:

a connecting hole defined penetrating the holder main body to communicate with inside of the tool installation groove;

a tool connecting member inserted through the connecting hole; and a locking portion defined in the medical tool so that the tool connecting member can be inserted therein and locked thereto.

9. The holder of claim 8, wherein the medical tool comprises a straight or curved impactor comprising the tool shaft and used in hip joint surgery, and the straight or curved impactor is provided with an impactor holding member which is coupled to the tool installation groove to movably support the straight or curved impactor, movably inserts the tool shaft therein, and is defined with the locking portion, and a stopper which restricts the movement of the tool shaft.

10. The holder of claim 9, wherein the stopper is configured as a stop pin defined in the tool shaft corresponding to a portion for connection with the impactor holding member, the impactor holding member comprises a cylindrical body inserted into the tool shaft and defined with the locking portion, and a movement elongated hole defined in a longitudinal direction of the cylindrical body and limiting the movement of the stop pin, and the locking portion comprises an introducing groove recessed in an inner end portion of the cylindrical body, and a locking groove extending curvedly from the introducing groove.

11. The holder of claim 8, wherein the medical tool is provided with the tool shaft, and comprises a straight or curved reamer used in hip joint surgery, the straight or curved reamer comprises a reamer frame having a hollow column structure to be externally put and installed on the tool shaft, and the reamer frame comprises the locking portion defined in a portion to be inserted in the tool installation groove, the locking portion comprising an introducing groove recessed in an inner end portion of the reamer frame, and a locking groove extending curvedly from the introducing groove.

* * * * *